US00PP08586P

United States Patent [19]

Stravers

[11] Patent Number: Plant 8,586

[45] Date of Patent: Feb. 8, 1994

[54] GERBERA PLANT: "TERALKO"

[75] Inventor: Lambertus J. M. Stravers, Kudelstaart, Netherlands

[73] Assignee: Terra Nigra B.V., De Kwakel, Netherlands

[21] Appl. No.: 942,277

[22] Filed: Sep. 9, 1992

[30] Foreign Application Priority Data

Nov. 2, 1990 [NL] Netherlands ..... GRB 1171

[51] Int. Cl.[5] ..... A01H 5/00

[52] U.S. Cl. ..... Plt./68.1

[58] Field of Search ..... Plt. 68.1

*Primary Examiner*—James R. Feyrer
*Assistant Examiner*—Elizabeth C. Kemmerer

[57] ABSTRACT

A new and distinct cultivar of Gerbera plant named 'Teralko', characterized by its single type, a distinctive very bright red ray floret which is a solid bright red color throughout, a green disc floret the outermost petaloids of which are red and display yellow stigmas and anthers, red perianth lobe color and 75 mm overall flower diameter is disclosed.

1 Drawing Sheet

BACKGROUND OF THE INVENTION

The present invention comprises a new and distinct cultivar of *Gerbera Jamesonni*, referred to by the cultivar name 'Teralko'. "Teralko' was originated from a hybridization program in De Kwakel, The Netherlands in 1989. The female parent was unnamed seedling M89.47, and the male parent was Tersalas -M89.16-. The female parent M89.47 has almost identical production, diameter, and heart color. However, it has a less bright red color and a shorter vase-life. The male parent has flowers with an almost identical diameter, but with a less brighter color red, a dark heart, a better production, and a shorter vase-life. Both had not been available outside Terra Nigra. The new cultivar was selected by me from the progeny of the stated parentage on or about March 1990. The first asexual reproduction of 'Teralko' was accomplished when vegetative cuttings were taken on April 1990 in De Kwakel. The new cultivar is presently being propagated by cuttings and tissue culture. Horticultural examination of selected units initiated November 1990 has demonstrated that the combination of characteristics as herein disclosed for 'Teralko' are firmly fixed and are retained through successive generations of asexual reproduction.

The following observations, measurements and comparisons describe plants grown in De Kwakel, The Netherlands, under greenhouse conditions which closely approximate those generally used in commercial practice. The following traits have been repeatedly observed and are determined to be basic characteristics of 'Teralko', which in combination distinguish this Gerbera from its parents and all other varieties of which I am aware:

1. Type: Single.
2. Color of ray floret: Very distinctive bright red.
3. Color of disc floret: Green.
4. Color of perianthy lobe: Red.
5. Diameter of flower head: Small 75 mm.

Of the many commercial cultivars known to me, there is no cultivar similar in comparison to 'Teralko'.

BRIEF DESCRIPTION OF THE FIGURE OF THE DRAWING

The accompanying photographic drawing shows typical inflorescence and foliage characteristics nearly true as possible. In the following description, color references are made to The Royal Horticultural Society Color Chart (R.H.S.). The color values were determined at approx. 11.00 a.m. on Mar. 15, 1991 under natural light at De Kwakel.

BOTANICAL DESCRIPTION OF THE PLANT

Botanical: *Gerbera jamessonii* cv Teralko.

1. INFLORESCENCE

A. Capitulum:
- *Form.*—Flat shaped.
- *Type.*—Single.
- *Diameter across face.*—75 mm.

B. Corolla of ray florets:
- *Color (general tonality from a distance of* 3 *meters-*).—Red.
- *Color (topside).*—RHS 43A-44B.
- *Color (bottom).*—RHS 32A.

C. Corolla of disc florets:
- *Color (mature).*—Green RHS 149B.
- *Color (immature).*—Green RHS 149B.

D. Reproductive organs:
- *Stigma.*—Yellow RHS 13C.
- *Anthers.*—Dark yellow RHS 14A.
- *Pappus.*—Yellow RHS 11B.

2. PLANT

A. General appearance:
- *Height.*—35 cm.

B. Foliage:
- *Color (abaxial).*—RHS 137A.
- *Color (adaxial).*—RHS 137C.
- *Shape.*—The shape of apex: Pointed. The margin of lobes: Sinuate.

C. Disease resistance: No special disease resistance.

3. OTHER CHARACTERISTICS

The following traits have been repeatedly observed and are determined to be basic characteristics of 'Teralko', which in combination distinguish this Gerbera as a new and distinct cultivar.

Leaf blade:

*Length.*—Short (45 cm).

*Width.*—Narrow (13 cm).

*Thickness*—Medium.

*Blistering.*—Medium.

*Pubescence.*—On upper side (midrib excluded): Medium.

*Depth of cuts or incisions in leaf.*—Basal part: Deep. Central part: Medium. Distal part: Shallow.

*Color.*—Upper side of the leaf blade is medium green (RHS 137A).

*Glossiness on upper side.*—Medium.

*Angle of apex.*—Weakly acute.

*Shape of apex.*—Pointed.

*Margin of lobes.*—Sinuate.

*Extensions of margin.*—Small.

*Petiole length.*—Medium.

*Petiole anthocyanin coloration.*—Present.

Peduncle:

*Length.*—Medium (60 cm).

*Cross section.*—Round.

*Tendency to fasciation.*—Absent.

*Thickness.*—Medium.

*Strength.*—Medium.

*Pubescence.*—Medium.

*Color.*—Medium green.

*Anthocyanin coloration.*—At base: Medium. At top: Absent.

*Involucral bracts.*—Absent.

Flower head:

*Type.*—Single.

*Diameter.*—Small (approx. 75 mm).

*Involucre.*—Height: Medium (14 mm). Diameter: Small. Number of bracts: Medium (48). Longitudinal axis of bracts of inner rows: Straight. Anthocyanin: Absent. Pubescence: Medium.

*Ray florets.*—Number: Medium (55). Shape: Narrow elliptic. Longitudinal axis outer row: Reflexing. Longitudinal axis inner row: Straight.

*Outer ray florets.*—Cross section: Convex. Length: Short (35 mm). Width: Narrow. Longitudinal folding: Medium. Angle of apex: Obtuse. Shape of apex: Rounded. Incisions of apex: Absent. Length of free petals: Short. Color distribution on inner side: Uniform. Edge of different color: Absent. Striation: Absent. Claw spot: Absent.

Disc florets:

*Diameters.*—Small.

*Main color perianth lobes.*—Red for both female and male flowers (RHS 45A).

Reproductive parts:

*Stigma.*—Main color yellow (RHS 13C).

*Anthers.*—Main color dark yellow (RHS 14A). Color of top relative to other parts is identical. Longitudinal striping: Absent.

*Pappus.*—Main color yellow (RHS 11B). Color of top relative to other parts is identical. Orientation: Level of top relative to closed disc florets is above.

*Fertility.*—Very good, around 200 pollen; the plant will form viable seed easily.

I claim:

1. A new and distinct cultivar of Gerbera plant names 'Teralko', as illustrated and described, characterized by its single type, a distinctive very bright red ray floret which is a solid bright red color throughout, a green disc floret the outermost petaloids of which are red and display yellow stigmas and anthers, red perianth lobe color and 75 mm overall flower diameter.

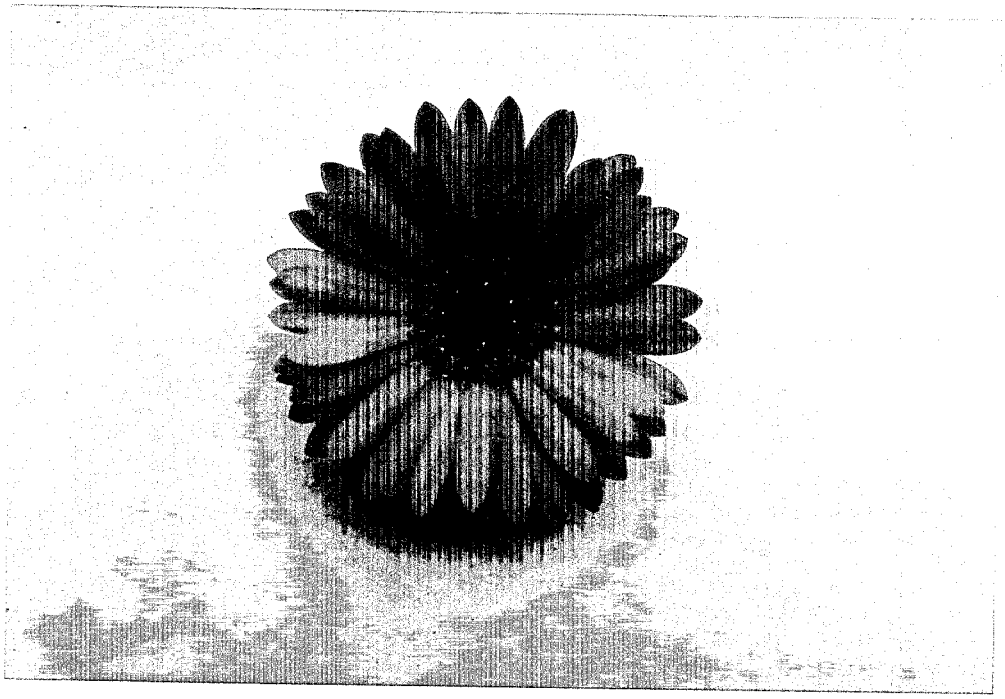

* * * * *